(12) United States Patent
DiCesare et al.

(10) Patent No.: US 8,882,785 B2
(45) Date of Patent: Nov. 11, 2014

(54) ENDOSCOPIC SUTURING DEVICE (76) Inventors: Paul C. DiCesare, Easton, CT (US);
Jeffrey P. Radziunas, Wallingford, CT (US)

( * ) Notice: Subject to any disclaimer, the term of this patent is extended or adjusted under 35 U.S.C. 154(b) by 664 days.

(21) Appl. No.: 13/121,213

(22) PCT Filed: Sep. 29, 2008

(86) PCT No.: PCT/US2008/011244
§ 371 (c)(1),
(2), (4) Date: Oct. 18, 2011

(87) PCT Pub. No.: WO2010/036227
PCT Pub. Date: Apr. 1, 2010

(65) Prior Publication Data
US 2012/0029536 A1    Feb. 2, 2012

(51) Int. Cl.
*A61B 17/04*    (2006.01)
(52) U.S. Cl.
CPC .................................. *A61B 17/0469* (2013.01)
USPC .......................................................... 606/144
(58) Field of Classification Search
USPC ............. 606/213, 139, 140, 144, 145; 600/37
See application file for complete search history.

(56) References Cited

U.S. PATENT DOCUMENTS

| | | | |
|---|---|---|---|
| 453,508 A | 6/1891 | Ruby | |
| 730,152 A | 6/1903 | Pitner | |
| 979,342 A | 12/1910 | Schaefer | |
| 1,325,699 A | 12/1919 | Oesterhaus | |
| 1,868,308 A | 7/1932 | Brumfield | |
| 2,170,599 A | 8/1939 | Stricklen | |
| 2,587,364 A | 2/1952 | Mitchell | |
| 2,601,852 A | 7/1952 | Wendt | |
| 2,621,655 A | 12/1952 | Olson | |

(Continued)

FOREIGN PATENT DOCUMENTS

| DE | 3909999 A1 | 9/1990 |
|---|---|---|
| EP | 0 598219 A2 | 10/1993 |

(Continued)

OTHER PUBLICATIONS

Bard Interventional Products Division, C. R. Bard, Inc., RapidFire™ Multiple Band Ligator—Information for Use', No. AE1904601/01, Issued Jun. 1996.

(Continued)

*Primary Examiner* — Gregory Anderson
*Assistant Examiner* — Christina Lauer
(74) *Attorney, Agent, or Firm* — Wolf, Greenfield & Sacks, P.C.

(57) ABSTRACT

An endoscopic suturing device that can be employed to suture tissue using endoscopic techniques to place one or more stitches in tissue during a single intubation of an endoscope. The suturing device may include a suturing capsule with a suction chamber that is configured to capture tissue that is to be sutured. A needle is movable along a pathway across the suction chamber to penetrate and place stitches in the captured tissue. A catch is located distal to the suction chamber to receive and retain the suture during a stitching sequence. The catch may be movable along the needle pathway and configured to release the suture when the catch moves a predetermined distance along the pathway. The catch may be configured so that a predetermined amount of force is required to move the catch the predetermined distance required to release the suture.

31 Claims, 8 Drawing Sheets

(56) References Cited

U.S. PATENT DOCUMENTS

| | | |
|---|---|---|
| 2,650,593 A | 9/1953 | Weil et al. |
| 2,880,728 A | 4/1959 | Rights |
| 3,013,559 A | 12/1961 | Thomas |
| 3,238,941 A | 3/1966 | Klein et al. |
| 3,470,875 A | 10/1969 | Johnson |
| 3,716,058 A | 2/1973 | Tanner |
| 3,757,781 A | 9/1973 | Smart |
| 3,760,810 A | 9/1973 | Hoorn |
| 3,845,772 A | 11/1974 | Smith |
| 3,858,571 A | 1/1975 | Rudolph |
| 4,126,124 A | 11/1978 | Miller |
| 4,144,876 A | 3/1979 | Deleo |
| 4,164,225 A | 8/1979 | Johnson et al. |
| 4,210,148 A | 7/1980 | Stivala |
| 4,216,777 A | 8/1980 | Pridemore |
| 4,226,239 A | 10/1980 | Polk et al. |
| 4,234,111 A | 11/1980 | Dischinger |
| 4,236,470 A | 12/1980 | Stenson |
| 4,291,698 A | 9/1981 | Fuchs et al. |
| 4,345,601 A | 8/1982 | Fukunda |
| 4,414,908 A | 11/1983 | Eguchi et al. |
| 4,415,092 A | 11/1983 | Boyer |
| 4,440,171 A | 4/1984 | Nomoto et al. |
| 4,469,101 A | 9/1984 | Coleman et al. |
| 4,474,174 A | 10/1984 | Petruzzi |
| 4,493,319 A | 1/1985 | Polk et al. |
| D279,504 S | 7/1985 | Tump |
| 4,597,390 A | 7/1986 | Mulhollan et al. |
| 4,607,620 A | 8/1986 | Storz |
| 4,615,472 A | 10/1986 | Nash |
| 4,621,640 A | 11/1986 | Mulhollan et al. |
| 4,637,816 A | 1/1987 | Mann |
| 4,665,906 A | 5/1987 | Jervis |
| 4,672,979 A | 6/1987 | Pohndorf |
| 4,706,653 A | 11/1987 | Yamamoto |
| 4,721,103 A | 1/1988 | Freedland |
| 4,735,194 A | 4/1988 | Stiegmann |
| 4,738,255 A | 4/1988 | Goble et al. |
| 4,741,330 A | 5/1988 | Hayhurst |
| 4,759,364 A | 7/1988 | Boebel |
| 4,794,911 A | 1/1989 | Okada |
| 4,825,259 A | 4/1989 | Berry, Jr. |
| 4,841,888 A | 6/1989 | Mills et al. |
| 4,860,746 A | 8/1989 | Yoon |
| 4,890,615 A | 1/1990 | Caspari et al. |
| 4,898,156 A | 2/1990 | Gatturna et al. |
| 4,899,743 A | 2/1990 | Nicholson et al. |
| 4,923,461 A | 5/1990 | Caspari et al. |
| 4,927,428 A | 5/1990 | Richards |
| 4,932,962 A | 6/1990 | Yoon et al. |
| 4,936,823 A | 6/1990 | Colvin et al. |
| 4,946,468 A | 8/1990 | Li |
| 4,950,285 A | 8/1990 | Wilk |
| 4,968,315 A | 11/1990 | Gatturna |
| 5,002,042 A | 3/1991 | Okada |
| 5,002,550 A | 3/1991 | Li |
| 5,037,021 A | 8/1991 | Mills et al. |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,078,731 A | 1/1992 | Hayhurst |
| 5,080,663 A | 1/1992 | Mills et al. |
| 5,100,417 A | 3/1992 | Cerier et al. |
| 5,100,418 A | 3/1992 | Yoon et al. |
| 5,100,421 A | 3/1992 | Christoudias |
| 5,102,421 A | 4/1992 | Anspach et al. |
| 5,116,349 A | 5/1992 | Aranyi |
| 5,123,913 A | 6/1992 | Wilk et al. |
| 5,125,553 A | 6/1992 | Oddsen et al. |
| 5,147,379 A | 9/1992 | Sabbaghian et al. |
| 5,152,769 A | 10/1992 | Baber |
| 5,163,945 A | 11/1992 | Ortiz et al. |
| 5,171,251 A | 12/1992 | Bregen et al. |
| 5,176,682 A | 1/1993 | Chow |
| 5,193,525 A | 3/1993 | Silverstein et al. |
| 5,199,566 A | 4/1993 | Ortiz et al. |
| 5,203,863 A | 4/1993 | Bidoia |
| 5,207,679 A | 5/1993 | Li |
| 5,207,690 A | 5/1993 | Rohrbacher |
| 5,207,694 A | 5/1993 | Broome |
| 5,211,650 A | 5/1993 | Node |
| 5,213,093 A | 5/1993 | Swindle |
| 5,217,486 A | 6/1993 | Rice et al. |
| 5,220,928 A | 6/1993 | Oddsen |
| 5,224,946 A | 7/1993 | Hayhurst et al. |
| 5,236,445 A | 8/1993 | Hayhurst et al. |
| 5,242,431 A | 9/1993 | Kristiansen |
| 5,254,126 A | 10/1993 | Filipi et al. |
| 5,258,015 A | 11/1993 | Li et al. |
| 5,258,016 A | 11/1993 | DiPoto et al. |
| 5,259,366 A | 11/1993 | Reydel et al. |
| 5,268,001 A | 12/1993 | Nicholson et al. |
| 5,269,789 A | 12/1993 | Chin et al. |
| 5,269,809 A | 12/1993 | Hayhurst et al. |
| 5,273,053 A | 12/1993 | Pohndorf |
| 5,281,236 A | 1/1994 | Bagnato et al. |
| 5,281,237 A | 1/1994 | Gimpelson |
| 5,282,832 A | 2/1994 | Toso et al. |
| 5,284,485 A | 2/1994 | Kammerer et al. |
| 5,290,296 A | 3/1994 | Phillips |
| 5,290,297 A | 3/1994 | Phillips |
| 5,297,536 A | 3/1994 | Wilk |
| 5,304,184 A | 4/1994 | Hathaway et al. |
| 5,306,280 A | 4/1994 | Bregen et al. |
| 5,306,309 A | 4/1994 | Wagner et al. |
| 5,312,438 A | 5/1994 | Johnson |
| 5,320,630 A | 6/1994 | Ahmed |
| 5,324,308 A | 6/1994 | Pierce |
| 5,330,442 A | 7/1994 | Green et al. |
| 5,330,486 A | 7/1994 | Wilk |
| 5,333,624 A | 8/1994 | Tovey |
| 5,334,200 A | 8/1994 | Johnson |
| 5,336,229 A | 8/1994 | Noda |
| 5,344,060 A | 9/1994 | Gravener et al. |
| 5,354,298 A | 10/1994 | Lee et al. |
| 5,356,413 A | 10/1994 | Martins et al. |
| 5,356,416 A | 10/1994 | Chu et al. |
| 5,364,407 A | 11/1994 | Poll |
| 5,364,408 A | 11/1994 | Gordon |
| 5,368,599 A | 11/1994 | Hirsch et al. |
| 5,368,601 A | 11/1994 | Sauer et al. |
| 5,370,662 A | 12/1994 | Stone et al. |
| 5,372,599 A | 12/1994 | Martins |
| 5,372,604 A | 12/1994 | Trott |
| 5,376,101 A | 12/1994 | Green et al. |
| 5,380,334 A | 1/1995 | Torrie et al. |
| 5,383,905 A | 1/1995 | Golds et al. |
| 5,389,103 A | 2/1995 | Melzer et al. |
| 5,391,173 A | 2/1995 | Wilk |
| 5,391,176 A | 2/1995 | Torre |
| 5,391,182 A | 2/1995 | Chin |
| 5,398,844 A | 3/1995 | Zaslavsky et al. |
| 5,403,346 A | 4/1995 | Loeser |
| 5,403,348 A | 4/1995 | Bonutti |
| 5,405,354 A | 4/1995 | Sarrett |
| 5,405,359 A | 4/1995 | Pierce |
| 5,409,499 A | 4/1995 | Yi |
| 5,411,506 A | 5/1995 | Goble et al. |
| 5,411,522 A | 5/1995 | Trott |
| 5,411,523 A | 5/1995 | Goble |
| 5,413,585 A | 5/1995 | Pagedas |
| 5,417,691 A | 5/1995 | Hayhurst |
| 5,417,697 A | 5/1995 | Wilk et al. |
| 5,417,699 A | 5/1995 | Klein et al. |
| 5,423,834 A | 6/1995 | Ahmed |
| 5,423,860 A | 6/1995 | Lizardi et al. |
| 5,431,639 A | 7/1995 | Shaw |
| 5,431,666 A | 7/1995 | Sauer et al. |
| 5,433,722 A | 7/1995 | Sharpe et al. |
| 5,437,680 A | 8/1995 | Yoon |
| 5,439,467 A | 8/1995 | Benderev et al. |
| 5,443,482 A | 8/1995 | Stone et al. |
| 5,445,167 A | 8/1995 | Yoon et al. |

(56) References Cited

U.S. PATENT DOCUMENTS

| | | |
|---|---|---|
| 5,447,512 A | 9/1995 | Wilson et al. |
| 5,458,608 A | 10/1995 | Wortrich |
| 5,462,558 A | 10/1995 | Kolesa et al. |
| 5,462,559 A | 10/1995 | Ahmed |
| 5,462,561 A | 10/1995 | Voda |
| 5,464,426 A | 11/1995 | Bonutti |
| 5,466,241 A | 11/1995 | Leroy et al. |
| 5,470,337 A | 11/1995 | Moss |
| 5,474,572 A | 12/1995 | Hayhurst |
| 5,474,573 A | 12/1995 | Hatcher |
| 5,478,353 A | 12/1995 | Yoon |
| 5,487,746 A | 1/1996 | Yu et al. |
| 5,507,754 A | 4/1996 | Green et al. |
| 5,507,758 A | 4/1996 | Thomason et al. |
| 5,507,797 A | 4/1996 | Suzuki et al. |
| 5,514,159 A | 5/1996 | Matula et al. |
| 5,520,700 A | 5/1996 | Beyar et al. |
| 5,520,702 A | 5/1996 | Sauer et al. |
| 5,520,703 A | 5/1996 | Essig et al. |
| 5,527,318 A | 6/1996 | McGarry |
| 5,531,763 A | 7/1996 | Mastri et al. |
| 5,542,432 A | 8/1996 | Slater |
| 5,545,170 A | 8/1996 | Hart |
| 5,545,180 A | 8/1996 | Le et al. |
| 5,549,617 A | 8/1996 | Green et al. |
| 5,562,686 A | 10/1996 | Sauer et al. |
| 5,562,689 A | 10/1996 | Green et al. |
| 5,569,274 A | 10/1996 | Rapacki et al. |
| 5,569,305 A | 10/1996 | Bonutti |
| 5,584,861 A | 12/1996 | Swain et al. |
| 5,584,862 A | 12/1996 | Bonutti |
| 5,591,177 A | 1/1997 | Lehrer |
| 5,591,180 A | 1/1997 | Hinchliffe |
| 5,601,530 A | 2/1997 | Neilsen et al. |
| 5,601,571 A | 2/1997 | Moss |
| 5,609,597 A | 3/1997 | Lehrer |
| 5,618,314 A | 4/1997 | Harwin et al. |
| 5,624,453 A | 4/1997 | Ahmed |
| 5,626,590 A | 5/1997 | Wilk |
| 5,626,614 A | 5/1997 | Hart |
| 5,630,824 A | 5/1997 | Hart |
| 5,645,553 A | 7/1997 | Kolesa et al. |
| 5,658,313 A | 8/1997 | Thal et al. |
| 5,665,109 A | 9/1997 | Yoon |
| 5,665,112 A | 9/1997 | Thal |
| 5,681,328 A | 10/1997 | Lamport et al. |
| 5,681,351 A | 10/1997 | Jamiolkowski et al. |
| 5,683,417 A | 11/1997 | Cooper |
| 5,683,419 A | 11/1997 | Thal |
| 5,683,464 A | 11/1997 | Wagner et al. |
| 5,693,060 A | 12/1997 | Martin |
| 5,695,505 A | 12/1997 | Yoon |
| 5,697,940 A | 12/1997 | Chu et al. |
| 5,702,397 A | 12/1997 | Goble et al. |
| 5,720,765 A | 2/1998 | Thal |
| 5,728,136 A | 3/1998 | Thal |
| 5,730,747 A | 3/1998 | Ek et al. |
| 5,735,793 A | 4/1998 | Takahashi et al. |
| 5,735,877 A | 4/1998 | Pagedes |
| 5,741,281 A | 4/1998 | Martin |
| 5,741,301 A | 4/1998 | Pagedes |
| 5,752,963 A | 5/1998 | Allard et al. |
| 5,755,730 A | 5/1998 | Swain et al. |
| 5,782,776 A | 7/1998 | Hani |
| 5,788,715 A | 8/1998 | Watson, Jr. et al. |
| 5,792,153 A | 8/1998 | Swain et al. |
| 5,810,853 A | 9/1998 | Yoon |
| 5,810,854 A | 9/1998 | Beach |
| 5,814,056 A | 9/1998 | Prosst et al. |
| 5,827,298 A | 10/1998 | Hart et al. |
| 5,827,306 A | 10/1998 | Yoon |
| 5,853,416 A | 12/1998 | Tolkoff |
| 5,860,946 A | 1/1999 | Hofstatter |
| 5,897,487 A | 4/1999 | Ouchi |
| 5,899,921 A | 5/1999 | Caspari et al. |
| 5,902,321 A | 5/1999 | Caspari et al. |
| 5,910,105 A | 6/1999 | Swain et al. |
| 5,919,208 A | 7/1999 | Valenti |
| RE36,289 E | 8/1999 | Le et al. |
| 5,931,844 A | 8/1999 | Thompson et al. |
| 5,935,149 A | 8/1999 | Ek |
| 5,938,586 A | 8/1999 | Wilk et al. |
| 5,947,983 A | 9/1999 | Solar et al. |
| 5,972,001 A | 10/1999 | Yoon |
| 5,984,917 A | 11/1999 | Fleischman et al. |
| 5,997,556 A | 12/1999 | Tanner |
| 6,001,110 A | 12/1999 | Adams |
| 6,007,551 A | 12/1999 | Peifer et al. |
| 6,010,515 A | 1/2000 | Swain et al. |
| 6,010,525 A | 1/2000 | Bonutti et al. |
| 6,015,428 A | 1/2000 | Padedas |
| 6,024,755 A | 2/2000 | Addis |
| 6,059,719 A | 5/2000 | Yamamoto et al. |
| 6,059,798 A | 5/2000 | Tolkoff |
| 6,066,160 A | 5/2000 | Colvin et al. |
| 6,071,233 A | 6/2000 | Ishikawa et al. |
| 6,071,292 A | 6/2000 | Makower et al. |
| 6,074,401 A | 6/2000 | Gardiner et al. |
| 6,086,600 A | 7/2000 | Kortenbach |
| 6,086,608 A | 7/2000 | Ek et al. |
| 6,099,535 A | 8/2000 | Lamport et al. |
| 6,126,677 A | 10/2000 | Ganaja et al. |
| 6,129,661 A | 10/2000 | Iafrati et al. |
| 6,136,009 A | 10/2000 | Mears |
| 6,149,658 A | 11/2000 | Gardiner et al. |
| 6,159,234 A | 12/2000 | Bonutti et al. |
| 6,200,329 B1 | 3/2001 | Fung et al. |
| 6,241,140 B1 | 6/2001 | Adams et al. |
| 6,280,452 B1 | 8/2001 | Mears |
| 6,358,259 B1 | 3/2002 | Swain et al. |
| 6,368,334 B1 | 4/2002 | Sauer |
| 6,436,108 B1 | 8/2002 | Mears |
| 6,514,265 B2 | 2/2003 | Ho et al. |
| 6,544,281 B2 | 4/2003 | ElAttrache et al. |
| 6,551,332 B1 | 4/2003 | Nguyen et al. |
| 6,607,541 B1 | 8/2003 | Gardiner et al. |
| 6,629,630 B2 | 10/2003 | Adams |
| 6,689,130 B2 | 2/2004 | Arai et al. |
| 6,719,763 B2 | 4/2004 | Chung et al. |
| 6,736,828 B1 | 5/2004 | Adams et al. |
| 6,997,931 B2 * | 2/2006 | Sauer et al. .................. 606/139 |
| 7,063,710 B2 | 6/2006 | Takamoto et al. |
| 7,220,266 B2 | 5/2007 | Gambale et al. |
| 7,442,198 B2 | 10/2008 | Gellman et al. |
| 7,704,264 B2 | 4/2010 | Ewers et al. |
| 2002/0177847 A1 | 11/2002 | Long et al. |
| 2003/0167062 A1 | 9/2003 | Gambale et al. |
| 2003/0171651 A1 | 9/2003 | Page et al. |
| 2003/0171760 A1 | 9/2003 | Gambale et al. |
| 2003/0176880 A1 | 9/2003 | Long et al. |
| 2003/0208209 A1 | 11/2003 | Gambale et al. |
| 2004/0034371 A1 | 2/2004 | Lehman et al. |
| 2004/0138704 A1 | 7/2004 | Gambale et al. |
| 2004/0158125 A1 | 8/2004 | Aznoian et al. |
| 2005/0033319 A1 * | 2/2005 | Gambale et al. .............. 606/139 |

FOREIGN PATENT DOCUMENTS

| | | |
|---|---|---|
| EP | 0 591991 A2 | 4/1994 |
| GB | 2165559 | 4/1986 |
| WO | WO 96/09796 | 4/1996 |
| WO | WO 96/20647 | 7/1996 |
| WO | WO 99/22650 | 5/1999 |
| WO | WO 01/66001 | 9/2001 |
| WO | WO 01/66018 | 9/2001 |
| WO | WO 01/87144 | 11/2001 |
| WO | WO 01/89370 | 11/2001 |
| WO | WO 01/89393 | 11/2001 |

OTHER PUBLICATIONS

Cook ® Wilson-Cook Medical GI Endoscopy, Sales Literature, www.wilsoncook.com.

Filipi, "Transoral, Flexible Endoscopic Suturing for Treatment of (56) References Cited

OTHER PUBLICATIONS

GERD: A Multicenter Trial", *Gastrointest Endosc* Apr. 2001; 53 (4): 416-422.

Lehman et al., "Endoscopic Gastroesophageal Suturing: Does Addition of Cautery Aid Plication Persistence?" *Digestive Disease Week* Poster Board Presentation—May 2000, On-line Abstract Feb. 2000.

Martinez-Sema et al., "Endoscopic Valvuloplasty for GERD", *Gastrointest Endosc* Nov. 2000; 52(5): 663-70.

Sherman et al., "Efficacy of Endoscopic Sphincterotomy and Surgical Sphincteroplasty for Patients with Sphincter of Oddi Dysfunction: Randomized, Prospective Study", *Gastrointest Endosc*, vol. 37, No. 2, 1991, p. 249 (Abstract).

Sherman et al., "Endoscopic Sphincterotomy Induced Hemorrhage: Treatment with Multipolar Electrocoagulation", *Gastrointest Endosc*, vol. 37, No. 2, 1991, p. 249 (Abstract).

International Search Report and Written Opinion for International application No. PCT/US2008/011244, dated Nov. 28, 2008.

\* cited by examiner

ENDOSCOPIC SUTURING DEVICE

BACKGROUND OF INVENTION

1. Field of Invention

The present invention relates to a device and methods for securing tissue of the human body, and more particularly relates to an endoscopic suturing device for endoscopically suturing tissue with minimally invasive techniques.

2. Discussion of Related Art

Endoscopic apposition devices can be used in the body of a patient without the need to make an external incision in the patient. The device is controlled outside the patient by endoscopic techniques. The device may comprise a sewing or stapling device for use in flexible endoscopy, although it is also applicable to devices for use in rigid endoscopy.

Endoscopic apposition devices have been found to be useful in the treatments of the digestive system, with the endoscope being transorally inserted through a patient's esophagus. In particular, such devices have been found useful in treating gastro-esophageal reflux disease (GERD) by placing stitches to form tissue plications at the junction of the esophagus and stomach. The minor anatomical change resulting from the plication formation appears to relieve the symptoms of GERD in some patients. It is also being proposed to employ such devices in treating obesity by placing stitches to segregate portions of a stomach or revise prior surgical procedures. It is also being proposed to employ such devices in treating obesity by placing stitches to segregate portions of a stomach or revise prior surgical procedures.

Endoscopic sewing devices of this general type are described in, for example, U.S. Pat. Nos. 5,080,663 and 5,792,153, which disclose a sewing device for passing a thread or suture through a tissue portion. The sewing device comprises a hollow needle movable between a first position in which it is out of the tissue portion and a second position in which it passes through the tissue portion, and a thread carrier adapted to be attached to the thread and being receivable within the hollow needle. The sewing device also comprises a body which defines a cavity within which the tissue portion can be held by suction. The hollow needle is mounted for movement in the body between the first and second positions.

The sewing devices include a single stitch sewing device and a multiple stitch sewing device. In the single stitch device, the thread carrier is transported by the needle through the tissue as the needle passes from its first position to its second position. When the needle returns to its first position, the thread carrier is maintained in the distal end of the sewing capsule. In the multiple stitch device, the same procedure occurs, but it is followed by a further step in which the hollow needle travels from its first position to its second position, picks up the thread carrier, and returns it to the first position. A second stitch may be formed during the next step. The sequence of steps is repeated as many times as may be required to form the desired number of stitches.

After placement of the sutures through the tissue, the suture can be secured tightly by knots or by a mechanical locking device. U.S. application Ser. No. 10/220,413 ("Suture Clips, Delivery Devices and Methods", filed Mar. 13, 2003) and Ser. No. 10/275,534 ("Tissue Capturing and Suturing Device and Method", filed Nov. 6, 2002), which are incorporated by reference herein in their entirety, disclose mechanical locking devices for securing a suture in an internal body location that are deliverable by an endoscope.

It would be desirable to provide an endoscopic tissue apposition device that can place multiple stitches in tissue during a single intubation.

SUMMARY

In one illustrative embodiment, an endoscopic tissue suturing device comprises a suturing capsule that is mountable to a distal end of an endoscope and is adapted to capture tissue at a tissue capture region thereof. The suturing device also comprises a needle that is slidable in a longitudinal direction within the suturing capsule along a pathway that extends from a proximal end of the tissue capture region to a distal end of the tissue capture region. The needle is adapted to penetrate tissue captured within the tissue capture region when the needle is extended in a distal direction from the proximal end to the distal end of the tissue capture region. The suturing device further comprises a suture tag that is securable to the needle to carry a suture across the tissue capture region, and a suture tag catch positioned distal to the tissue capture region to retain the suture tag at a distal end of the tissue capture region when the suture tag is released from the needle and the needle is retracted to the proximal end of the tissue capture region. The suture tag catch is movable in the longitudinal direction to release the suture tag when the suture tag is locked to the needle and the needle is retracted toward the proximal end of the tissue capture region.

In another illustrative embodiment, an endoscopic tissue suturing device comprises a suturing capsule that is mountable to a distal end of an endoscope and includes a tissue suction chamber that is adapted to capture tissue therein when a vacuum is applied thereto. The suturing device also comprises a needle that is slidable within the suturing capsule along a pathway that extends from a first end of the tissue suction chamber to a second end of the tissue suction chamber. The needle is adapted to penetrate tissue captured within the tissue suction chamber when the needle is extended from the first end to the second end of the tissue suction chamber. The suturing device further comprises a suture tag that is securable to the needle to carry a suture across the tissue suction chamber, and a suture tag catch positioned at the second end of the tissue suction chamber to retain the suture tag when the suture tag is released from the needle and the needle is retracted to the first end of the tissue suction chamber. The suture tag catch is movable both along the pathway and transverse to the pathway to release the suture tag when the suture tag is locked to the needle and the needle is retracted to the first end of the tissue suction chamber.

BRIEF DESCRIPTION OF DRAWINGS

Various embodiments of the invention will now be described, by way of example, with reference to the accompanying drawings, in which.

DETAILED DESCRIPTION

The present invention is directed to an endoscopic suturing device that can be employed to suture tissue using endoscopic techniques. The suturing device may be used to place one or more stitches in tissue during a single intubation of an endoscope. The suturing device may be detachably mounted to any of various conventional endoscopes, although aspects of the device may be integrated with an endoscope configured specifically for endoscopic suturing procedures.

The suturing device may include a suturing capsule that is configured to capture tissue that is to be sutured. In one embodiment, the capsule is mountable to the distal end of an endoscope. The capsule may include a suction chamber into which is drawn tissue via a vacuum. However, the device may employ other arrangements for capturing tissue as would be apparent to one of skill in the art.

The suturing device may include a needle to penetrate and place a suture through captured tissue. The needle may be positioned in the capsule through a working channel of the endoscope. The needle may be arranged so that it can be moved along a pathway across the suction chamber to penetrate and place stitches in the captured tissue. However, the device may employ other needle arrangements as would be apparent to one of skill in the art.

The suturing device may include a catch that is located distal to the suction chamber to receive and retain the suture during a stitching sequence. In one embodiment, the catch is movable along the needle pathway and configured to release the suture when the catch moves a predetermined distance along the pathway. The needle and the catch may be configured to move in a longitudinal direction. The catch may be positioned coaxial with the needle.

The catch may be configured so that a predetermined amount of force is required to move the catch the predetermined distance required to release the suture. Such an arrangement may reduce inadvertent release of the suture from the catch during a stitching sequence. In one embodiment, the catch may be biased in a distal direction away from the needle toward a locked position to retain the suture. The catch may be opened to release the suture by moving the catch in a proximal direction against the distally directed biasing force to its unlocked position.

The suturing device may include a suture tag that is attached to the suture. The suture tag facilitates passage of the suture through tissue and retention of the suture by the catch. In this regard, the suture tag may be carried by the needle through tissue and into the catch. A locking arrangement may be provided to secure the suture tag to the needle and to release the suture tag from the needle during the stitching sequence.

The catch may be configured to receive the suture tag when the needle is extended distally across the suction chamber and into the catch, and then retain the suture tag when the suture tag lock is unlocked and the needle is withdrawn proximally from the catch and retracted across the chamber. In this regard, the catch may be configured to strip the suture tag from the needle.

The catch may include a tag locking clip that is configured to receive and retain the suture tag. In one embodiment, the clip may include at least a pair of resilient fingers that are configured to open and close in a direction transverse to the needle pathway to receive and retain the suture tag. In one embodiment, the fingers may be configured to open and close in a lateral or radial direction relative to the pathway. The fingers may be configured so that they are biased in an inward lateral or radial direction to a closed position to retain the suture tag and expand outwardly to an open position against the lateral or radial biasing force to receive and release the tag. However, the device may employ other catch arrangements to retain and release the suture tag as would be apparent to one of skill in the art.

The catch may employ a cam arrangement configured to open the catch and release the suture tag. In one embodiment, the cam arrangement is configured to open the resilient fingers when the tag locking clip is moved the predetermined distance along the needle pathway. The cam arrangement may include a cam tube with a tapered cam surface that is engaged by and coacts with corresponding cam surfaces provided on the resilient fingers. Each of the resilient fingers may include an offset bend along a portion thereof that forms the cam surface for engaging the tapered cam surface of the cam tube. However, the device may employ other arrangements to open the catch as would be apparent to one of skill in the art.

In one embodiment, the suture tag may be configured to be supported and secured about the exterior surface of the needle. A suture tag lock may be provided between the suture tag and the needle with the lock being actuatable between a locked position to secure the suture tag to the needle and an unlocked position to release the suture tag from the needle. The suture tag lock may include a locking sleeve that is actuatable between the locked and unlocked positions by expanding and reducing a portion of the sleeve by way of relative sliding movement between the needle and sleeve.

Figure 1:
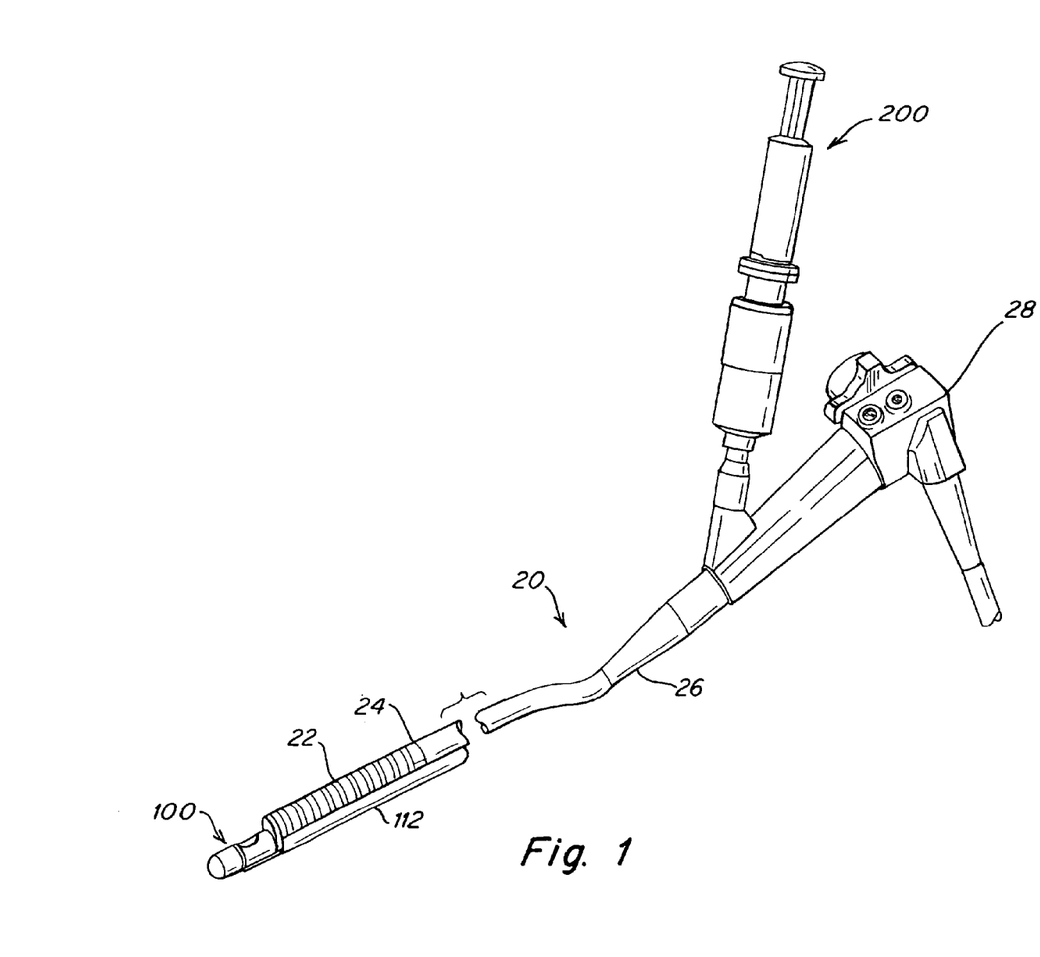
FIG. 1 is a perspective view of an endoscopic suturing device according to one illustrative embodiment employed with an endoscope.

In one illustrative embodiment shown in FIG. 1, the endoscopic suturing device 20 includes a suturing capsule 100 that is releasably secured to the distal end 22 of an endoscope 24. The device also includes a needle (not shown) that passes through a working channel of the endoscope and into the capsule. The suturing device is operated by a control handle 200 releasably mounted to the proximal end 26 of the endoscope. As shown, the control handle may be mounted adjacent the endoscope control handle 28. The suturing device operates to place sutures through tissue at internal locations within a patient accessible by an endoscope.

Figure 2:
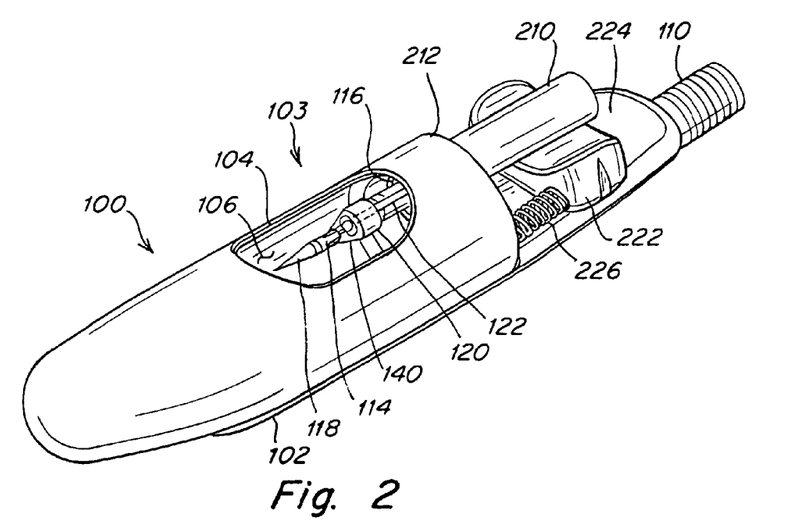
FIG. 2 is a perspective view of a suturing capsule according to one illustrative embodiment of the suturing device of FIG. 1.
Figure 3:
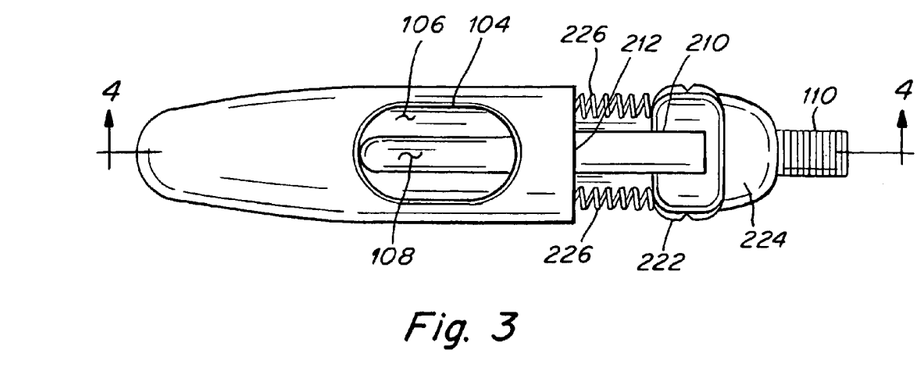
FIG. 3 is a top plan view of the suturing capsule of FIG. 2.
Figure 4:
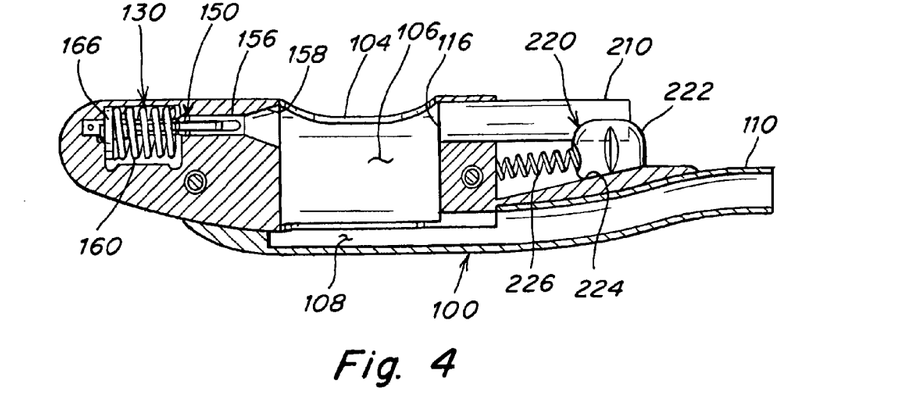
FIG. 4 is a cross sectional view of the suturing capsule taken along section line 4-4 of FIG. 3.

In one illustrative embodiment shown in FIGS. 2-4, the suturing capsule 100 includes a cylindrical body 102 having an atraumatic shape to reduce the chance of trauma to internal tissues during an endoscopic suturing procedure. The capsule is similar in configuration and operation to a capsule disclosed in U.S. Pat. Publication 2005/0033319, which is incorporated herein by reference.

The capsule may include a tissue capture region 103 that is configured to capture tissue. In one illustrative embodiment, the capsule includes a suction port 104 that opens to a tissue suction chamber 106 into which tissue portions to be sutured may be collected via a vacuum introduced into the chamber. As shown in FIG. 3, an elongated channel 108 is provided at the bottom of the suction chamber for introducing negative pressure (i.e., vacuum) to the suction chamber 106 to selectively capture a tissue portion that is to be sutured. The vacuum is introduced to the channel 108 through vacuum tube 110 extending proximally from the capsule 100 and joined to a separate vacuum line 112 (FIG. 1) that extends along the exterior of the endoscope.

The capsule is configured to receive a needle 114 that is slidable through a needle track 116 formed through the capsule. The needle may include a solid shaft with a sharpened distal tip 118 that is joined at its proximal end to a pusher shaft (not shown) that extends proximally from the suture capsule, through the working channel of the endoscope. When the needle is moved longitudinally through the needle track, it passes through and traverses the suction chamber 106 so that tissue suctioned into the chamber will be penetrated by the distally advancing needle.

The pusher shaft exits the proximal end of the endoscope where it may be joined to and manipulated by the control handle 200. One example of a control handle that may be particularly suited for use with the suturing device is disclosed in US 2005/0033319.

The needle may be employed to place a suture through tissue drawn into the suction chamber. In one illustrative embodiment shown in FIG. 2, the needle 114 carries an annular suture tag 120 that fits closely about the outside surface of the needle. A suture 122 is joined to the suture tag to be carried through a suctioned tissue portion when the needle carrying the suture tag is advanced distally. The suturing device may be configured to selectively secure and release the suture tag to and from the needle.

The suturing device may be configured so that full distal advancement of the needle places the suture tag 120 within a suture tag catch 130 located distal to the suction chamber. After penetrating a captured tissue portion and entering the suture catch, the suture tag 120 may be released and the needle withdrawn proximally leaving behind the suture tag in the suture tag catch.

The suture tag catch 130 may be configured to release the suture by moving the catch a predetermined distance in the longitudinal direction. The suture tag catch 130 may also be configured so that movement of the catch to release the suture tag requires the application of a predetermined axial force to the catch.

Figure 5:
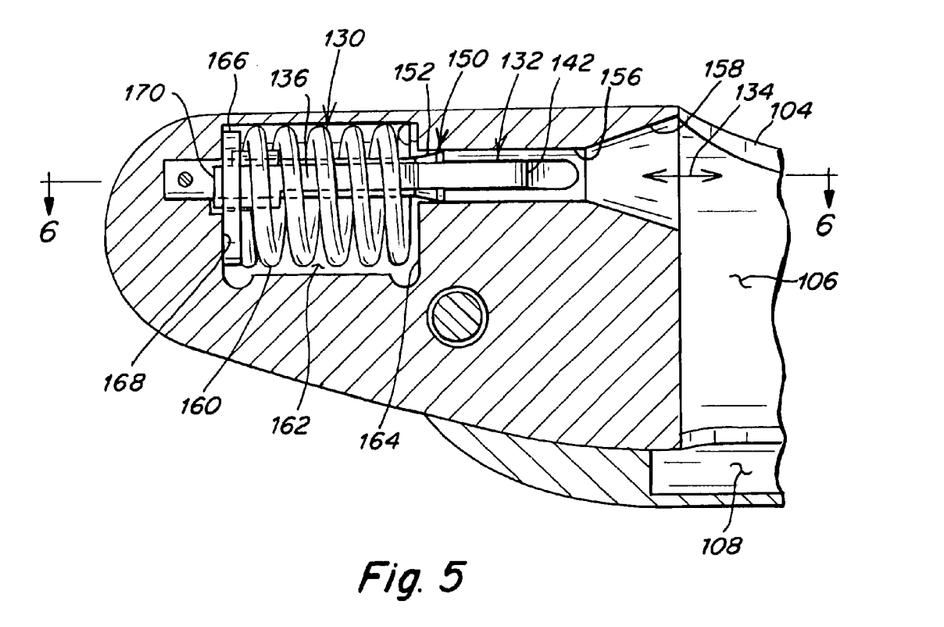
FIG. 5 is an enlarged view of a suture tag catch according to one illustrative embodiment employed with the suturing capsule of FIGS. 2-4.
Figure 6:
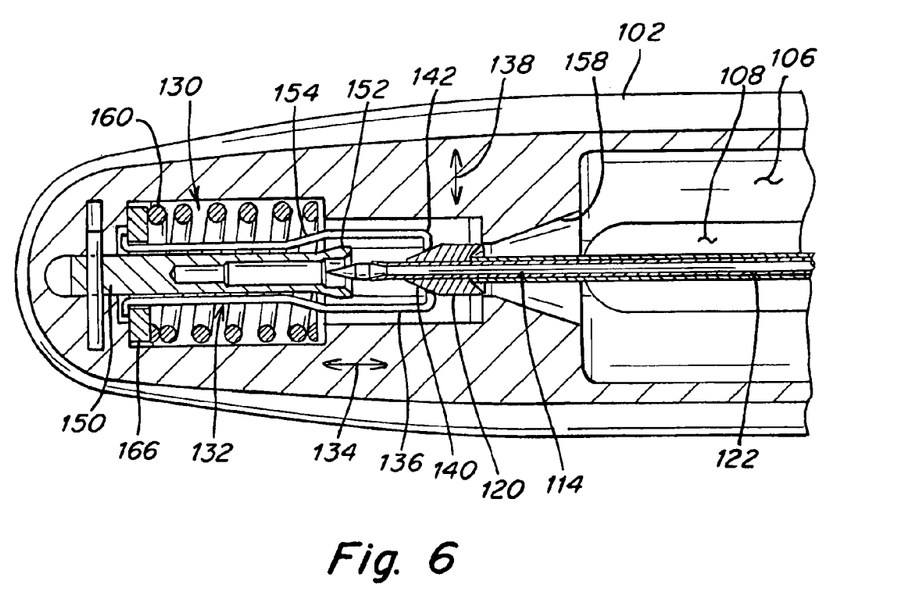
FIG. 6 is a cross sectional view of the suture tag catch taken along section line 6-6 of FIG. 5 illustrating the needle being extended distally toward the catch.

In one illustrative embodiment shown in FIGS. 4-6, the suture tag catch 130 includes a tag locking clip 132 that is movable in the longitudinal direction 134. The locking clip 132 includes a plurality of fingers 136 that are movable between a closed or locked position to secure the suture tag and an open or unlocked position to release the suture tag from the catch. The locking clip may employ resilient fingers 136 that are self-biasing inwardly in a lateral or radial direction 138 (FIG. 6) to the closed or locked position to secure the suture tag within the catch. In this manner, the fingers are movable in both the longitudinal and lateral directions to secure and release the suture tag.

One or both of the suture tag and the tag locking clip may be configured to facilitate insertion of the suture tag into the catch. In one illustrative embodiment shown in FIGS. 6-7, the suture tag 120 has a tapered or conically shaped distal end portion 140 that expands the locking fingers 136 outwardly (illustrated by arrow 139) as the needle and the suture tag are extended in the distal direction into the catch. The tips 142 of the resilient fingers may be provided with a tapered edge 144 (FIG. 11) that coact with the suture tag to facilitate opening the fingers and allow passage of the suture tag into the catch. The tapered distal end 140 also creates a low profile that may facilitate passage of the suture tag through tissue as the needle and suture tag are advanced distally through the tissue.

Figure 8:
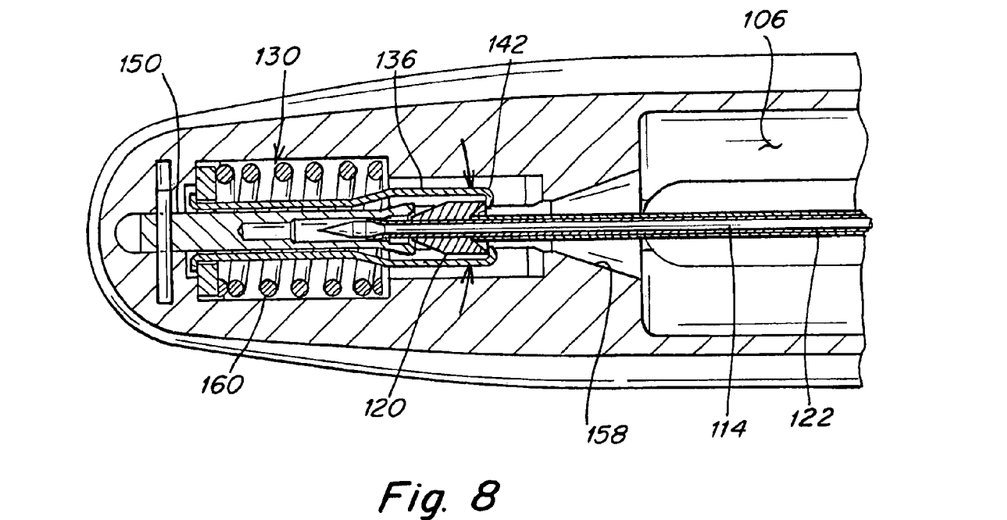
FIG. 8 illustrates the suture tag being fully advanced into the suture tag catch with the suture tag clip in a closed position to secure the suture clip.

As shown in FIG. 8, the locking fingers 136 return to the closed or locked position behind the suture tag 120 once the needle has been fully extended in the distal direction into the catch. In this locked position, the suture tag 120 is retained by and cannot be removed from the catch until a predetermined axial force is exerted in the proximal direction to withdraw the suture tag from the catch.

Figure 9:
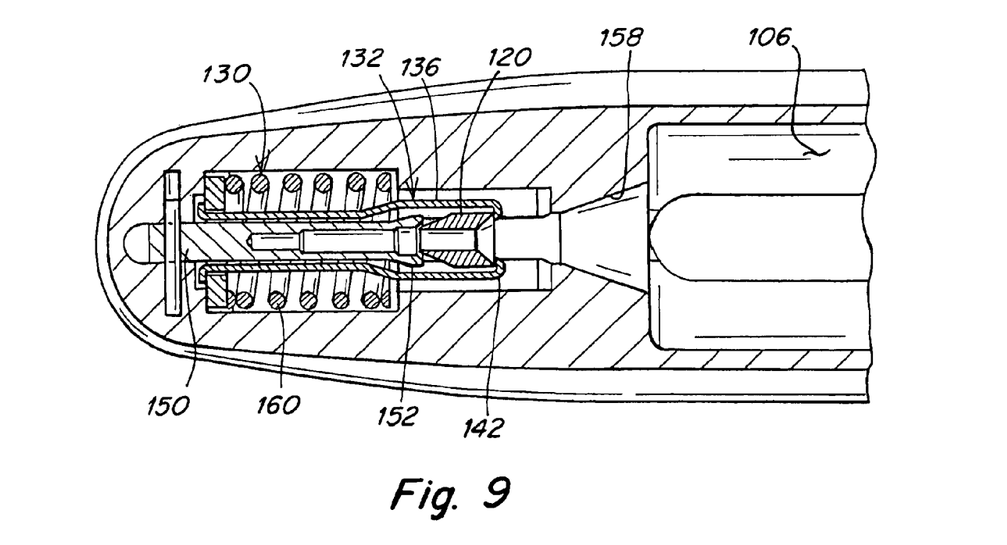
FIG. 9 illustrates the needle having been withdrawn proximally from the suture tag catch with suture tag retained by the suture tag clip.

As shown in FIG. 9, with the suture tag 120 secured within the catch 130, the suture tag can be unlocked from the needle and the needle withdrawn across the chamber, thereby stripping the suture tag from the needle and retaining the tag at the distal end of the chamber with the catch.

After capture and release of the suture tag in the suture tag catch 130, the needle may be withdrawn proximally and the tissue released from the suction chamber 106 with a suture 122 left passing through the tissue (not shown) and having one end joined to the captured suture tag 120 within the catch and the other end of the suture extending into the needle track 116, through the working channel of the endoscope and exiting the proximal end of the endoscope.

Figure 10:
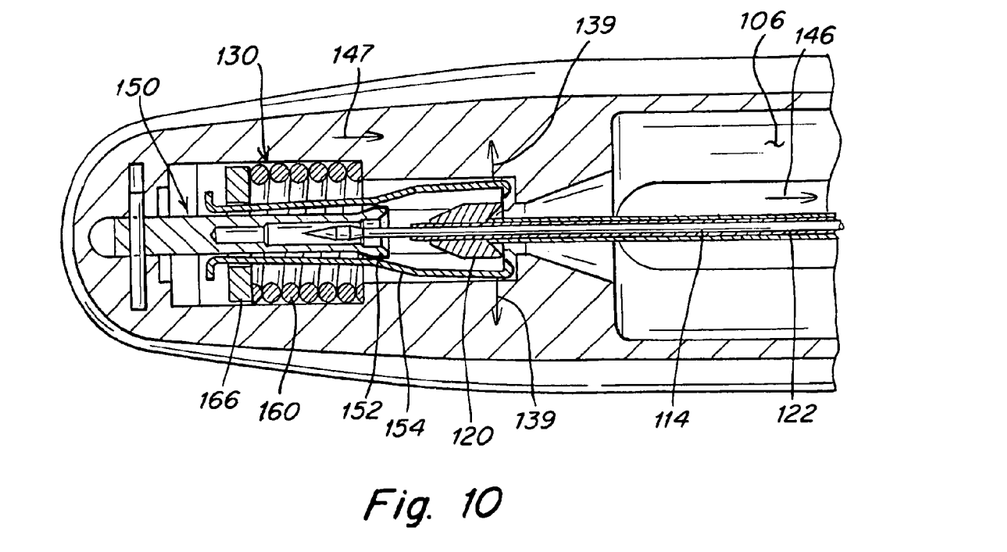
FIG. 10 illustrates the suture tag clip being drawn in the proximal direction by the needle and the suture tag with the clip being opened to release the suture tag.

As shown in FIG. 10, to release the suture tag from the suture tag catch, the needle 114 is extended into the catch 130 and the suture tag 120 is secured to the needle. With the suture tag secured, the needle can be retracted in the proximal direction 146 causing the tag locking clip 132, which is gripping the secured suture tag, to similarly move in the proximal direction 147. The suture tag catch 130 may be configured so that drawing the tag locking clip 132 in the proximal direction opens the locking fingers to release the suture tag 120 from the catch.

Figure 11:
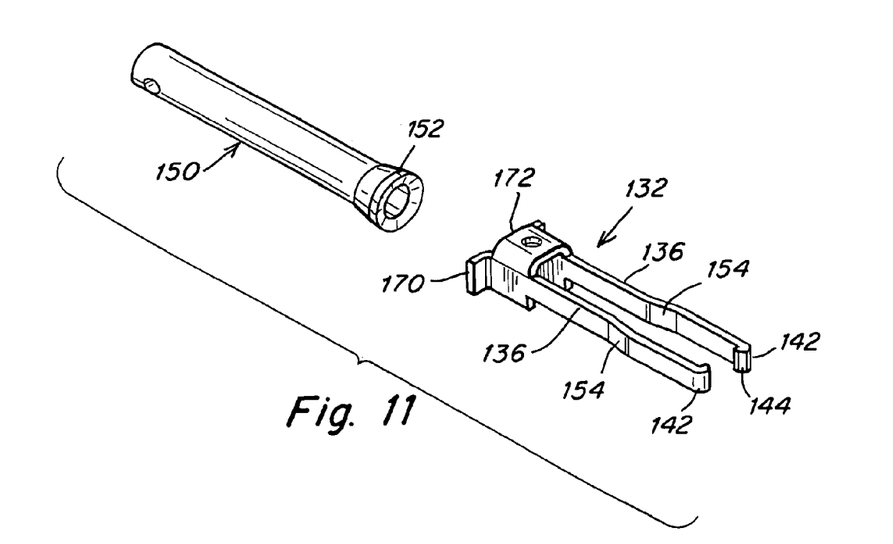
FIG. 11 is an exploded perspective view of the suture tag clip and a cam arrangement for the suture tag catch according to one illustrative embodiment.

In one illustrative embodiment shown in FIG. 11, the suture tag catch 130 employs a cam arrangement to open the tag locking clip. The cam arrangement includes a cam tube 150 with an external cam surface 152 that co-acts with a cam follower 154 provided on each of the locking fingers 136 to expand the locking clip to an open position once the locking clip is drawn a predetermined distance in the proximal direction. The cam surface 152 is located at the proximal end of the tube and tapers outwardly in the proximal direction to expand the locking fingers 136 as the clip is drawn in the proximal direction. The cam follower 154 includes an offset bend formed in each locking finger 136 that engages and interacts with the cam surface 152 of the tube to spread open the fingers of the locking clip. Similar to the cam surface, the offset bend 154 is angled outwardly in the proximal direction.

In one embodiment, the cam surface has a taper of approximately 15° and the cam follower has an offset bend angle of approximately 12°. It is to be appreciated, however, that other arrangements may be used to open the tag locking clip to release the suture tag from the catch, as would be apparent to one of skill in the art.

As shown in FIGS. 5-6, the cam tube 150 is supported within the capsule and maintained in axial alignment with the needle. The cam tube may be configured to receive at least a portion of the needle 114 therein (FIGS. 7-8) when the needle is extended into the suture tag catch. The capsule may provided with an elongated channel 156 that is aligned with and receives the needle 114 as the needle is extended across the suction chamber 106 and into the catch 130. As shown, the proximal end of the cam tube 150 is supported in the distal end of the channel 156 and the elongated fingers 136 extend in the proximal direction along a portion of the channel toward the suction chamber.

During operation, the needle 114 may potentially angle off and become misaligned with the suture tag catch 130 as the needle 114 penetrates and is driven through tissue. To facilitate alignment with and insertion of the needle 114 into the suture tag catch 130, the capsule may be provided with a needle guide that directs a misaligned needle into the channel and the suture tag catch. In one illustrative embodiment shown in FIG. 5, the guide 158 includes a conical surface at the proximal end of the channel 156. As shown, the conical surface 158 tapers inwardly in a direction from the proximal end toward the distal end of the channel so that a misaligned needle will be funneled into the channel.

The catch may be configured so that drawing the tag locking clip the predetermined distance in the proximal direction to release the locking fingers requires a predetermined amount of force to overcome the locking force of the catch. The catch may be configured so that the grip force of the fingers is greater than the release force of the catch.

In one embodiment, the suture tag catch is configured with a release force having a range of approximately 0.75-2.0 lbs applied in a straight axial direction. Preferably, the release force is approximately 1.0 lbs. It is to be appreciated, however, that the catch may be configured to require any suitable release force as would be apparent to one of skill in the art.

It may be desirable to configure the suture tag catch so that it securely retains the suture tag as a suture attached to the tag is pulled or otherwise manipulated through tissue with the suturing device. In this regard, the suturing capsule arrangement requires a suture to pull on the suture tag at an angle relative to the axial release direction of the catch during a suturing procedure. This arrangement requires that the suture apply a relatively large force on the suture tag to generate sufficient force in the axial direction to release the tag from the catch.

In one illustrative embodiment shown in FIGS. 4-5, the retention force of the catch is created with a compression spring 160 that exerts a force against the base of the catch clip to bias the clip in the distal direction. As shown, the spring 160 is located within a cavity 162 of the capsule with one end of the spring engaging a proximal wall 164 of the cavity and the other end of the spring engaging a spacer 166 provided between the spring and a distal wall 168 of the cavity. As shown in FIGS. 5 and 11, the catch clip 132 includes a pair of ears 170 that engage the opposite side of the spacer 166 and pull the spacer in the proximal direction to compress the spring as the catch clip is drawn proximally by the suture tag.

In one embodiment, the suture tag catch 130 is configured so that the spring 160 applies a preload of approximately 1.9 lbs on the clip with the clip in its locked position. A clip displacement in the axial direction of approximately 0.030-0.040 inches is required to sufficiently open the clip to release the suture tag. The spring 160 is a coil spring with a spring rate of approximately 9.91 lbs/in with a free length of approximately 0.25 inches and an outer diameter of approximately 0.148 inches. The spring is formed of spring tempered stainless steel, type 316, wire having a diameter of approximately 0.016 inches. It is to be appreciated, however, that the spring may be fabricated from any suitable material and in other configurations to provide desired loading properties as would apparent to one of ordinary skill in the art.

In one illustrative embodiment shown in FIG. 11, the tag locking clip 132 includes a U-shaped base 172 with the pair of fingers 136 extending from opposite sides of the base. The fingers extend longitudinally in a proximal direction terminating in a free-end having an inwardly curved tip 142 to catch the proximal facing surface after the tag has entered the catch.

The catch clip 132 may be formed from a sheet of hardened stainless steel, type 304, having a thickness of approximately 0.010 inches. The material has a hardness of Rockwell C 40-45. The clip is formed by bending the sheet into the desired shape. It is to be appreciated, however, that the clip may be configured in other suitable shapes and fabricated from any suitable material using other techniques as would be apparent to one of ordinary skill in the art.

As indicated above, the suturing device may be configured to selectively secure and release the suture tag to and from the needle. In one illustrative embodiment shown in FIGS. 12-13, a suture tag lock 180 releasably and selectively secures the suture tag 120 about the outside surface of the needle 114. The suture tag lock 180 is remotely operable from the proximal end of the endoscope with the control handle 200. The suture tag lock includes a locking sleeve 182 through which extends the needle. A portion of the locking sleeve may be configured to expand and contract in response to relative movement between the needle and the locking sleeve to secure and release the suture tag.

Figure 12:
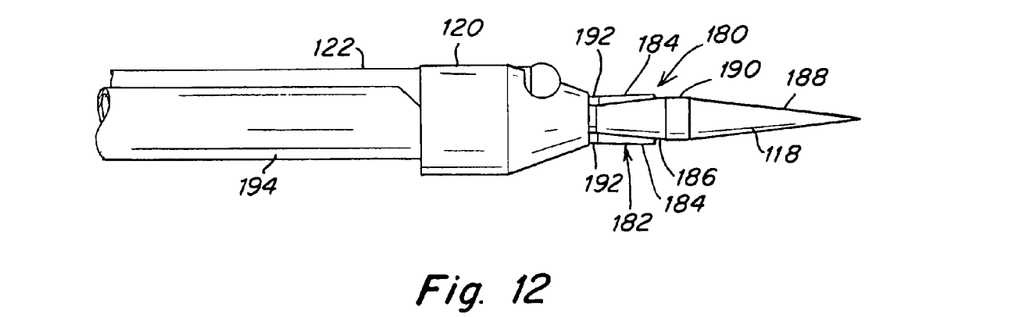
FIG. 12 is a side view of the needle with a suture tag lock according to one illustrative embodiment shown in a locked position to secure the suture tag to the needle.
Figure 13:
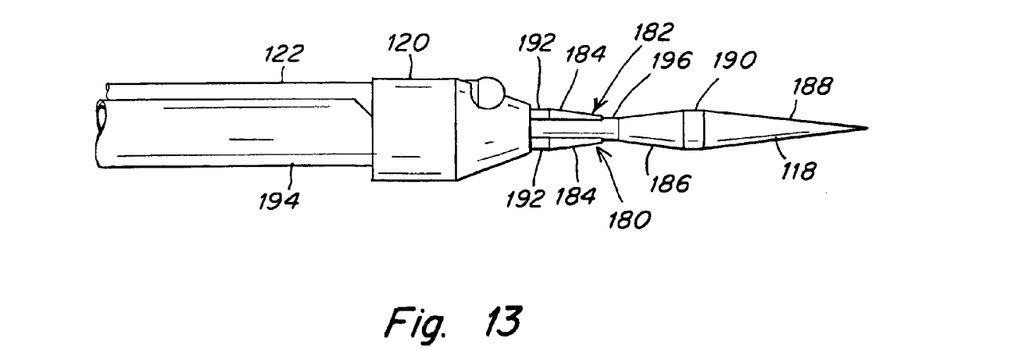
FIG. 13 illustrates the suture tag lock in an unlocked position to release the suture tag from the needle.

In one illustrative embodiment shown in FIGS. 12-13, the distal end of the locking sleeve 182 includes resilient locking splines 184 that are configured to move in a radial direction to secure and release the suture tag. As described below, the locking splines cooperate with the needle to increase and decrease the diameter of the locking sleeve relative to the through bore of the suture tag to secure and release the suture tag to and from the needle.

As shown in FIGS. 12-13, the distal end of the needle has a generally spear-like shape with a proximal increasing barrel taper 186 converging with a distal increasing barrel taper 188 to create an enlarged portion of the tip 190.

As shown in FIG. 12, when the needle is withdrawn proximally into the locking sleeve 182 of the suture tag lock, the locking splines 184 ride over the proximal barrel taper 186 of the needle 114 and expand radially outward to create locking surfaces 192 that prevent distal sliding of the suture tag 120 over the needle. The splayed splines 184 effectively increases the profile of the locking sleeve to an extent that the suture tag 120 cannot fit over it, thereby locking the suture tag in place on the needle. A stiffening sleeve 194, which has a diameter larger than the bore of the suture tag, may be provided to prevent the suture tag 120 from sliding proximally relative to the needle and the locking sleeve.

To release the suture tag so that it may slide distally relative to the needle as would be desired when leaving the tag in the suture tag catch 130 during suturing procedure, the needle 114 is moved distally relative to the locking sleeve 182. As shown in FIG. 13, movement of the needle distally relative to the locking sleeve moves the proximal barrel taper 186 away from the splines 184 so that a reduced diameter of the needle shaft 196 underlies the splines which then resiliently conform to the reduced diameter shaft. In this manner, the profile of the locking sleeve is effectively reduced to an extent that the suture tag 120 can be removed from the needle. The enlarged portion 190 of the needle, without the added thickness of the two splines 184 of the locking sleeve, has a profile over which the suture tag 120 may pass freely.

The locking sleeve 182 is slidable over the shaft of the needle 114. In one embodiment, the locking sleeve is a stainless steel hypotube having an inner diameter of approximately 0.016 inch sized to fit closely over the outside surface of the needle shaft, which has a diameter of approximately 0.0155 inch. It is to be understood that other suture tag lock arrangements are contemplated and may be employed as would be apparent to one of skill in the art.

As indicated above, the capsule may be joined to the distal end of an endoscope. In one illustrative embodiment shown in FIGS. 2-4, the capsule 100 includes a proximally extending guide tube 210 that is inserted into the working channel of the endoscope. The guide tube 210 is rigid and extends proximally from the proximal end 212 of the capsule to protrude a short distance into the working channel of the endoscope. The guide tube is open to receive the needle during operation.

Figure 14:
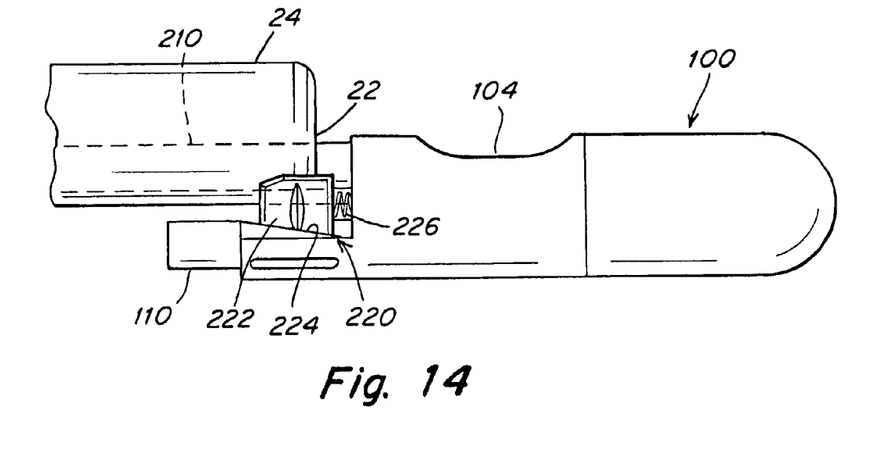
FIG. 14 is a side view of the suturing capsule of FIGS. 2-4 mounted to the distal end of an endoscope.

In one illustrative embodiment shown in FIG. 14, the capsule may be secured to the distal end of the endoscope with a reverse wedge securement mechanism. A reverse wedge and an endoscopic accessory securement mechanism is fully described in U.S. Pat. No. 6,869,395, issued Mar. 22, 2005, and titled "Endoscopic Accessory Attachment Mechanism", which is incorporated herein by reference in its entirety.

The reverse wedge securement mechanism 220 includes a wedge 222 that is slidable along an angled ramp 224 to become wedged between the distal end 22 of the endoscope 24 and the ramp surface as it slides up the ramp 224. Leverage against the distal end of the endoscope is maintained by the presence of the guide tube 210 through the working channel. One or more return springs 226 maintain force against the wedge 222 to bias the wedge upward along the ramp 224 and maintain wedge contact with the endoscope. It is to be appreciated that the capsule may be secured to an endoscope using other suitable arrangements apparent to one of skill in the art.

In one embodiment, the suture capsule body may be fabricated from a rigid material, such as stainless steel. It is to be understood, however, that the capsule body may be fabricated from other suitable materials apparent to one of skill in the art.

In one illustrative embodiment, operation of the suture tag catch 130 to retain and release the suture tag is described below with reference to FIGS. 6-10.

As shown in FIG. 6, after capturing tissue (not shown), the needle 114 is extended across suction chamber 106 through the tissue and enters the tag locking clip 132 with the suture tag 120 approaching the inwardly projecting tips 142 of the resilient fingers 136.

Figure 7:
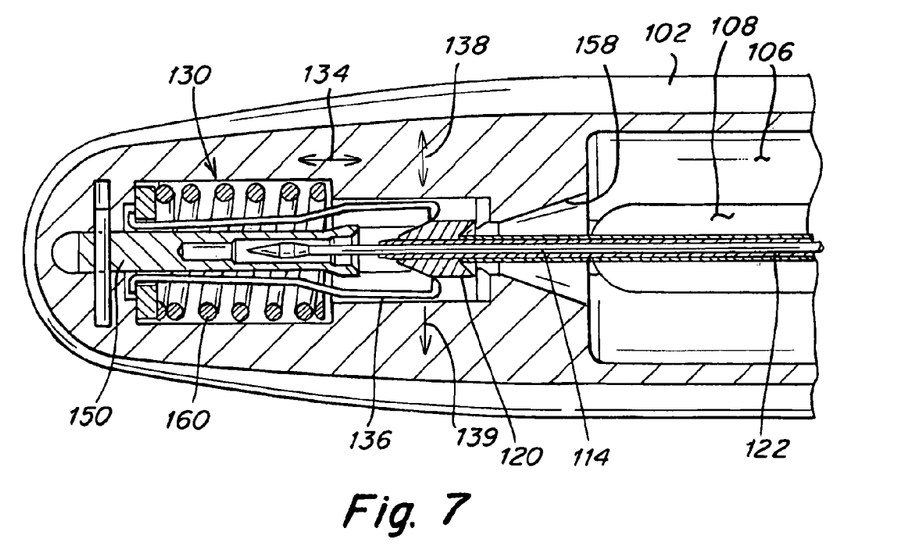
FIG. 7 illustrates the suture tag expanding the suture tag clip to an open position as the needle is extended further into the suture tag catch.

As shown in FIG. 7, as the needle proceeds distally, the sharpened distal tip 118 of the needle enters the cam tube 150 and the suture tag 120 engages and spreads apart the resilient fingers 136 to allow entry of the suture tag into the catch.

As shown in FIG. 8, once the suture tag 120 is advanced fully into the catch, the fingers 136 close so that the inwardly projecting tips 142 are located behind and engage the proximal end of the suture tag to secure the tag in the catch.

After the suture tag 120 is secured by the catch, the suture tag lock 180 may be actuated to unlock the suture tag from the needle 114. As described above, the suture tag lock is unlocked by advancing the needle 114 distally relative to the locking sleeve 182 to reduce the effective profile of the locking splines 184. As shown in FIG. 9, the needle (not shown) is withdrawn from the suture tag 120 as the needle is retracted in the proximal direction from the catch.

After the captured tissue is released, the needle may be extended distally across the suction chamber and into the catch. The suture tag lock 180 is then locked to secure the suture tag to the needle by withdrawing the needle into the locking sleeve 182, thereby expanding the locking splines 184 to increase the effective profile of the splines.

As shown in FIG. 10, with the suture tag 120 secured to the needle 114, the needle may be retracted in the proximal direction. Because the suture tag is still secured by the catch, the suture tag clip 132 similarly is drawn in the proximal direction by the needle. When the suture tag clip 132 has been drawn a predetermined distance, the fingers 136 of the clip coact with the cam tube 150 and open to release the suture tag 120 from the catch.

As indicated above, the suturing device may be employed with any of various conventional endoscopes. As would be understood by one of ordinary skill in the art, an endoscope conventionally includes a working channel and a viewing channel that extend along the length of the elongated shaft of the endoscope. An endoscope may also include other channels that can be used for a light source or a liquid cleaning source.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An endoscopic tissue suturing device, comprising:
a suturing capsule that is mountable to a distal end of an endoscope, the suturing capsule adapted to capture tissue at a tissue capture region thereof;
a needle that is slidable in a longitudinal direction within the suturing capsule along a pathway that extends from a proximal end of the tissue capture region to a distal end of the tissue capture region, the needle is adapted to penetrate tissue captured within the tissue capture region when the needle is extended in a distal direction from the proximal end to the distal end of the tissue capture region;
a suture tag that is securable to the needle to carry a suture across the tissue capture region; and
a suture tag catch positioned distal to the tissue capture region to retain the suture tag at a distal end of the tissue capture region when the suture tag is released from the needle and the needle is retracted to the proximal end of the tissue capture region, the suture tag catch being movable relative to the suturing capsule in the longitudinal direction to release the suture tag when the suture tag is locked to the needle and the needle is retracted toward the proximal end of the tissue capture region.

2. The endoscopic tissue suturing device according to claim 1, wherein the suturing capsule includes a tissue suction chamber at the tissue capture region that is adapted to capture tissue therein when a vacuum is applied thereto.

3. The endoscopic tissue suturing device according to claim 1, wherein the suture tag catch is slidable in a proximal direction toward the proximal end of the tissue capture region to release the suture tag.

4. The endoscopic tissue suturing device according to claim 3, wherein the suture tag catch is biased to a locked position in a distal direction away from the proximal end of the tissue capture region.

5. The endoscopic tissue suturing device according to claim 4, further comprising a compression spring positioned between a distal end of the suture tag catch and the distal end of the tissue capture region to bias the suture tag catch in the distal direction.

6. The endoscopic tissue suturing device according to claim 1, wherein the suture tag catch includes a plurality of resilient fingers that expand in an outward lateral direction to receive and release the suture tag.

7. The endoscopic tissue suturing device according to claim 6, wherein the resilient fingers are biased inwardly to a locked position to retain the suture tag when the suture tag is received in the suture tag catch.

8. The endoscopic tissue suturing device according to claim 7, wherein the suture tag is configured to expand the resilient fingers outwardly to receive the suture tag as the needle is extended toward the distal end of the tissue capture region.

9. The endoscopic tissue suturing device according to claim 8, wherein the suture tag includes a tapered distal end configured to expand the resilient fingers.

10. The endoscopic tissue suturing device according to claim 8, further comprising a cam tube that is configured to open the resilient fingers as the suture tag catch is moved in the proximal direction.

11. The endoscopic tissue suturing device according to claim 10, wherein the cam tube includes a tapered surface at a proximal end thereof that is adapted to engage and open the resilient fingers.

12. The endoscopic tissue suturing device according to claim 11, wherein each resilient finger includes a follower that is configured to coact with the tapered surface.

13. The endoscopic tissue suturing device according to claim 12, wherein the follower includes an offset bend in the resilient finger.

14. The endoscopic tissue suturing device according to claim 10, wherein the cam tube is adapted to receive the needle when the needle is extended toward the distal end of the tissue capture region.

15. The endoscopic tissue suturing device according to claim 6, wherein the resilient fingers are configured to grasp a proximal end of the suture tag to retain the suture tag in the suture tag catch, the resilient fingers being pulled in the proximal direction by the suture tag when the suture tag is locked to the needle and the needle is retracted in the proximal direction toward the proximal end of the tissue capture region, movement of the needle a predetermined distance causes the resilient fingers to open to release the suture tag.

16. An endoscopic tissue suturing device, comprising:
a suturing capsule that is mountable to a distal end of an endoscope, the suturing capsule including a tissue suction chamber that is adapted to capture tissue therein when a vacuum is applied thereto;
a needle that is slidable within the suturing capsule along a pathway that extends from a first end of the tissue suction chamber to a second end of the tissue suction chamber, the needle being adapted to penetrate tissue captured within the tissue suction chamber when the needle is extended from the first end to the second end of the tissue suction chamber;
a suture tag that is securable to the needle to carry a suture across the tissue suction chamber; and
a suture tag catch positioned at the second end of the tissue suction chamber to retain the suture tag when the suture tag is released from the needle and the needle is retracted to the first end of the tissue suction chamber, the suture tag catch being movable both along the pathway and transverse to the pathway to release the suture tag when the suture tag is locked to the needle and the needle is retracted to the first end of the tissue suction chamber.

17. The endoscopic tissue suturing device according to claim 16, wherein the suture tag catch is movable in a linear direction along the pathway and in a lateral direction transverse to the linear direction.

18. The endoscopic tissue suturing device according to claim 17, wherein the needle is movable in a longitudinal direction along the pathway.

19. The endoscopic tissue suturing device according to claim 16, wherein the suture tag catch is slidable in a first direction toward the first end of the tissue suction chamber to release the suture tag.

20. The endoscopic tissue suturing device according to claim 19, wherein the suture tag catch is biased to a locked position in a second direction away from the first end of the tissue suction chamber.

21. The endoscopic tissue suturing device according to claim 20, further comprising a compression spring positioned between a second end of the suture tag catch and the second end of the tissue suction chamber to bias the suture tag catch in the second direction.

22. The endoscopic tissue suturing device according to claim 16, wherein the suture tag catch includes a plurality of resilient fingers that expand in an outward lateral direction to receive and release the suture tag.

23. The endoscopic tissue suturing device according to claim 22, wherein the resilient fingers are biased inwardly to a locked position to retain the suture tag when the suture tag is received in the suture tag catch.

24. The endoscopic tissue suturing device according to claim 23, wherein the suture tag is configured to expand the resilient fingers outwardly to receive the suture tag as the needle is extended toward the second end of the tissue suction chamber.

25. The endoscopic tissue suturing device according to claim 24, wherein the suture tag includes a tapered distal end configured to expand the resilient fingers.

26. The endoscopic tissue suturing device according to claim 24, further comprising a cam tube that is configured to open the resilient fingers as the suture tag catch is moved in the first direction.

27. The endoscopic tissue suturing device according to claim 26, wherein the cam tube includes a tapered surface at a first end thereof that is adapted to engage and open the resilient fingers.

28. The endoscopic tissue suturing device according to claim 27, wherein each resilient finger includes a follower that is configured to coact with the tapered surface.

29. The endoscopic tissue suturing device according to claim 28, wherein the follower includes an offset bend in the resilient finger.

30. The endoscopic tissue suturing device according to claim 26, wherein the cam tube is adapted to receive the needle when the needle is extended toward the second end of the tissue suction chamber.

31. The endoscopic tissue suturing device according to claim 22, wherein the resilient fingers are configured to grasp a first end of the suture tag to retain the suture tag in the suture tag catch, the resilient fingers being pulled in the first direction by the suture tag when the suture tag is locked to the needle and the needle is retracted in the first direction toward the first end of the tissue suction chamber, movement of the needle a predetermined distance causes the resilient fingers to open to release the suture tag.

* * * * *